United States Patent [19]

Wallace et al.

[11] Patent Number: 5,958,444
[45] Date of Patent: Sep. 28, 1999

[54] METHOD FOR TREATING URINARY REFLUX

[75] Inventors: George Wallace, Coto De Caza, Calif.; Richard J. Greff, St. Pete Beach, Fla.

[73] Assignee: Micro Therapeutics, Inc., Irvine, Calif.

[21] Appl. No.: 08/874,677

[22] Filed: Jun. 13, 1997

[51] Int. Cl.⁶ .................................. A61F 2/00; A61F 2/04
[52] U.S. Cl. .......................... 424/430; 424/426; 424/423; 424/422; 600/30; 623/12; 523/113; 514/953
[58] Field of Search .................................. 424/422, 423, 424/430, 426; 514/953; 523/113; 623/12; 600/30

[56] References Cited

U.S. PATENT DOCUMENTS

| | | |
|---|---|---|
| 4,631,188 | 12/1986 | Stoy et al. . |
| 5,007,940 | 4/1991 | Berg . |
| 5,336,263 | 8/1994 | Ersek et al. . |
| 5,580,568 | 12/1996 | Greff et al. . |
| 5,667,767 | 9/1997 | Greff et al. . |
| 5,785,642 | 7/1998 | Wallace et al. . |

OTHER PUBLICATIONS

Leonard et al., "Endoscopic Injection of Glutaraldehyde Cross–linked Bovine Dermal Collagen for Correction of Vesicoureteral Reflux", J. Urol., 145:115–119 (1991).
Atala et al., "Endoscopic Treatment of Vesicoureteral Reflux with a Self–Detachable Balloon System", J. Urol., 148:724–728 (1992).
Atala et al., "Endoscopic Treatment of Vesicoureteral Reflux with a Chondrocyte–Alginate Suspension", J. Urol., 152:641–643 (1994).
Frey et al., "Histological Behavior of Glutaraldehyde Cross–linked Bovine Collagen Injected into the Human Bladder for the Treament of Vesicoureteral Reflux", J. Urol. 152:632–635 (1994).
Frey et al., "Suburetal Collagen Injection for the Endoscopic Treatment of Vesicoureteral Reflux in Children. Followup Study of 97 Treated Ureters and Histological Analysis of Collagen Implants", J. Urol., 148:718–723 (1992).
Atala et al., "Laparoscopic Correction of Vesicoureteral Reflux", J. Urol., 150:748–751 (1993).
Capozza et al., "Endoscopic Treatment of Vesico–Ureterica Reflux and Urinary Incontinence: Technical Problems in the Paediatric Patient", British J. Urol., 75:538–542 (1995).
Atala et al., "Injectable Alginate Seeded with Chondrocytes as a Potential Treatment for Vesicoureteral Reflux", J. Urol., 150:745–747 (1993).
Leonard et al., "Local Tissue Reaction to the Subureteral Injection of Glutaraldehyde Cross–linked Bovine Collagen in Humans", J. Urol., 143:1209–1212 (1990).
Kinugasa, et al., "Direct Thrombosis of Aneurysms with Cellulose Acetate Polymer", J. Neurosurg., 77:501–507 (1992).
Kinugasa, et al., "Early Treatment of Subarachnoid Hemorrhage After Preventing Rerupture of an Aneurysm", J. Neurosurg., 83:34–41 (1995).
Kinugasa, et al., "Prophylactic Thrombosis to Prevent New Bleeding and to Delay Aneurysm Surgery", Neurosurg., 36:661 (1995).
Taki, et al., "Selection and Combination of Various Endovascular Techniques in the Treatment of Giant Aneurysms", J. Neurosurg., 77:37–42 (1992).
Park, et al., "New Polymers for Therapeutic Embolization", Poster #47, Meeting of Radiological Society of North America (1993).
Meriguerian et al., "Submucosal Injection of Polyvinyl Alcohol Foam in Rabbit Bladder", J. Urol., 144:531–533 (1990).
Walker, et al., "Injectable Bioglass as a Potential Substitute for Injectable Polytetrafluoroethylene", J. Urol., 148:645 (1992).

*Primary Examiner*—Thurman K. Page
*Assistant Examiner*—Brian K. Seidleck
*Attorney, Agent, or Firm*—Burns, Doane, Swecker & Mathis, LLP

[57] ABSTRACT

Disclosed are methods for treating vesicoureteral reflux in a mammal wherein a composition comprising a water insoluble biocompatible polymer and a biocompatible solvent is delivered to the subureteral tissue of the mammal.

22 Claims, No Drawings

METHOD FOR TREATING URINARY REFLUX

BACKGROUND OF THE INVENTION

Field of the Invention

This invention is directed to methods for treating vesicoureteral reflux in mammals generally and humans in particular. In these methods, a composition comprising a biocompatible polymer, a biocompatible solvent, and a contrast agent is delivered to the subureteral region of a mammal.

The biocompatible polymer is selected to be soluble in the biocompatible solvent, but insoluble in fluids of the subureteral region. The biocompatible solvent is miscible/soluble in the fluids of this tissue and, upon contact with such fluids, the biocompatible solvent quickly diffuses away whereupon the biocompatible polymer precipitates to form an occlusion or implant in the subureteral region which compresses the ureter thereby increasing resistance to retrograde urine flow into the ureter from the bladder.

REFERENCES

The following publications are cited in this application as superscript numbers:

[1] Leonard et al., "*Endoscopic Injection of Glutaraldehyde Cross-linked Bovine Dermal Collagen for Correction of Vesicoureteral Reflux*", J. Urol., 145:115–119 (1991).

[2] Atala et al., "*Endoscopic Treatment of Vesicoureteral Reflux with a Self-Detachable Balloon System*", J. Urol., 148:724–728 (1992).

[3] Atala et al., "*Endoscopic Treatment of Vesicoureteral Reflux with a Chondrocyte-Alginate Suspension*", J. Urol., 152:641–643 (1994).

[4] Frey et al., "*Histological Behavior of Glutaraldehyde Cross-linked Bovine Collagen Injected into the Human Bladder for the Treatment of Vesicoureteral Reflux*", J. Urol. 152:632–635 (1994).

[5] Frey et al., "*Subureteral Collagen Injection for the Endoscopic Treatment of Vesicoureteral Reflux in Children. Followup Study of 97 Treated Ureters and Histological Analysis of Collagen Implants*", J. Urol., 148:718–723 (1992).

[6] Atala et al., "*Laparoscopic Correction of Vesicoureteral Reflux*", J. Urol., 150:748–751 (1993).

[7] Capozza et al., "*Endoscopic Treatment of Vesico-Ureteric Reflux and Urinary Incontinence: Technical Problems in the Paediatric Patient*", British J. Urol., 75:538–542 (1995).

[8] Atala et al., "*Injectable Alginate Seeded with Chondrocytes as a Potential Treatment for Vesicoureteral Reflux*", J. Urol., 150:745–747 (1993).

[9] Leonard et al., "*Local Tissue Reaction to the Subureteral Injection of Glutaraldehyde Cross-linked Bovine Collagen in Humans*", J. Urol., 143:1209–1212 (1990).

[10] Kinugasa, et al., "*Direct Thrombosis of Aneurysms with Cellulose Acetate Polymer*", J. Neurosurg., 77:501–507 (1992).

[11] Kinugasa, et al., "*Early Treatment of Subarachnoid Hemorrhage After Preventing Rerupture of an Aneurysm*", J. Neurosurg., 83:34–41 (1995).

[12] Kinugasa, et al., "*Prophylactic Thrombosis to Prevent New Bleeding and to Delay Aneurysm Surgery*", Neurosurg., 36:661 (1995).

[13] Greff, et al., U.S. Pat. No. 5,558,068 for "Cellulose Diacetate Compositions for Use in Embolizing Blood Vessels", issued Dec. 3, 1997.

[14] Greff, et al., allowed U.S. patent application Ser. No. 08/507,863 for "Novel Compositions for Use in Embolizing Blood Vessels", filed Jul. 27, 1995.

[15] Taki, et al., "*Selection and Combination of Various Endovascular Techniques in the Treatment of Giant Aneurysms*", J. Neurosurg., 77:37–42 (1992).

[16] Park, et al., "*New Polymers for Therapeutic Embolization*", Poster #47, Meeting of Radiological Society of North America (1993).

[17] Meriguerian, et al., "*Submucosal Injection of Polyvinyl Alcohol Foam in Rabbit Bladder*", J. Urol., 144:531–533 (1990).

[18] Walker, et al., "*Injectable Bioglass as a Potential Substitute for Injectable Polytetrafluoroethylene*", J. Urol., 148:645 (1992).

All of the above references are herein incorporated by reference in their entirety to the same extent as if each individual reference was specifically and individually indicated to be incorporated herein by reference in its entirety.

State of the Art

Vesicoureteral reflux (urinary reflux) is a condition wherein urine moves from the bladder into the ureters and sometimes the renal pelvis during voiding or with elevated pressure in the bladder. Vesicoureteral reflux is common in children with anatomic abnormalities of the urinary tract, however, it also occurs in children with anatomically normal but infected urinary tracts.

Normally, the junction of the terminal ureter with the urinary bladder provides a competent sphincter so that during micturition urine leaves the bladder only via the urethra. Reflux occurs when there is inadequate intravesical submucosal tunnel (valve mechanism) or defective attachment of the ureter to the bladder. Thus, an anatomically impaired vesicoureteral junction facilitates reflux of urine and bacteria into the ureters and results in upper tract infection and renal damage.

The initial treatment of vesicoureteral reflux usually consists of suppressive antibiotics in anticipation of spontaneous resolution. Thus, reflux of minor degree may disappear with standard treatment for intercurrent urinary infection, i.e., antibiotics. For more severe degrees of reflux and minor reflux unresponsive to antibiotics, surgical correction is usually necessary. However, open surgical repair has a well recognized morbidity, which consists of pain and immobilization of a lower abdominal incision, as well as the attendant risks of surgery in general, e.g., anesthesia.

An alternative to open surgery which reduces the morbidity of vesicoureteral reflux correction would be of significant clinical benefit. Such a technique has been developed over the last 25 years and is termed endoscopic subureteral injection.

Endoscopic subureteral injection is a simple procedure in which a substance is injected into the subureteral region, usually on an outpatient basis. The injected substance implants in the subureteral region and enhances its bulk. In turn, the enhanced bulk of the subureteral region narrows the ureteral orifice[5] thereby inhibiting retrograde urine flow. Hence, the ideal injected substance used as an implant material should be non-migratory, conserve its volume, be non-antigenic and be able to be delivered endoscopically. To date, endoscopic subureteral injection of various substances has had varying results.

For example, polytetrafluorethylene (Teflon™) was one of the first substances utilized.[7] However, Teflon™ induces a granulomatous reaction and is capable of migration to distant areas such as the pelvic lymph nodes, spleen, lungs and brain. These observations have cast doubt on the applicability of use in humans of Teflon™.

Another substance that has been utilized is glutaraldehyde cross-linked bovine dermal collagen[4,5,9]. The major problem with the use of collagen in the treatment of reflux is that the implant is biodegradable and, hence, volume size of the implant decreases with time. This has made re-treatment necessary. Collagen is also quite viscous and therefore difficult to inject.

Another injectable substance that has been used for the treatment of vesicoureteral reflux is a chondrocyte-alginate suspension.[3,6,8] Chondrocytes, cells capable of synthesizing cartilage, were harvested from animals, mixed with alginate to form a gel that was subsequently injected into the subureteral region of the animal. Although encouraging results have been seen, use of this suspension requires a biopsy in order to harvest the chondrocytes with the patient having to return at a later date to undergo treatment with the autologous chondrocyte-alginate suspension.

Various other injectable substances have been reported or proposed as implant materials for the treatment of bladder conditions, such as vesicoureteral reflux. These substances include polyvinyl alcohol foam,[17] glass particles,[18] and a detachable silicone balloon.[2]

Additionally, misplacement of the implant, either distal or lateral to the ureteral orifice, usually in a position inadequate to provide support for the submucosal tunnel[1,9], has been a problem with all of the above mentioned substances.

In view of the above, it is evident that there is a need for treatment methods of vesicoureteral reflux in mammals which methods would allow an implant (occlusion)-forming substance to be accurately injected into the subureteral region and which implant-forming substance would preferably be delivered endoscopically, conserve its volume in vivo, be non-migratory and be substantially non-immunogenic.

The present invention is directed to the disco very that vesicoureteral reflux can be treated in mammals by injecting sufficient amounts of a composition comprising a biocompatible water insoluble polymer and a biocompatible solvent to the subureteral region under conditions such that a polymer precipitate forms in situ in the subureteral region. This polymer precipitate forms an implant which compresses the ureter opening thereby increasing resistance to retrograde urine flow into the ureters during voiding and decreasing reflux in the mammal. The polymeric compositions of this invention are non-biodegradable and, accordingly, do not substantially decrease in volume over time. Moreover, the injection process provides for a coherent implant mass, not particulates, which mass is non-migratory.

In a preferred embodiment, a contrast agent is employed in the composition to permit monitoring of the injection by conventional methods, e.g., fluoroscopy, to ensure proper placement. Moreover, when a water insoluble contrast agent is employed, this contrast agent becomes incorporated in the precipitate (implant) formed in situ thereby allowing post-injection monitoring of the implant by conventional methods to ensure correct retention of the implant months or even years after injection. Conventional monitoring methods include, by way of example, fluoroscopy, ultrasound, and in some cases visual detection.

SUMMARY OF THE INVENTION

This invention is directed to the discovery that unexpected and surprising results are achieved when mammals with vesicoureteral reflux are treated with a composition comprising a biocompatible water insoluble polymer and a biocompatible solvent. In particular, deficiencies associated with the prior art procedures are reduced by the invention. Such deficiencies include, for example, problems associated with migration of particulates over time and the biodegradation of the injected mass (e.g., collagen type materials) employed to form an occlusion in the periurethral tissue of the mammal.

Accordingly, in one of its method aspects, this invention is directed to a method for treating vesicoureteral reflux in a mammal, which method comprises delivering a composition comprising a water insoluble biocompatible polymer and a biocompatible solvent to the subureteral region of the mammal wherein said delivery is conducted under conditions such that a polymer precipitate forms in situ in the subureteral region thereby reducing the vesicoureteral reflux in the mammal.

In preferred aspects of this invention, the composition further comprises a contrast agent which then permits monitoring the accurate delivery of such compositions to the subureteral region. If the contrast agent is a water insoluble agent, post-delivery monitoring of the implant in the patient can be conducted for months, years after injection.

Accordingly, in a particularly preferred embodiment, this invention is directed to a method for treating vesicoureteral reflux in a mammal, which method comprises delivering a composition comprising a water insoluble biocompatible polymer, a contrast agent and a biocompatible solvent to the subureteral region of the mammal wherein said delivery is conducted under conditions such that a polymer precipitate forms in situ in the subureteral region thereby reducing the vesicoureteral reflux in the mammal.

Even more preferably, the contrast agent is a water insoluble contrast agent.

Post-injection monitoring also permits the physician to conduct additional injections of the implant forming composition into the patient as the clinical condition dictates in order to further reduce urinary reflux in the mammalian patient. Accordingly, in another method aspect, this invention is directed to a method for the delivery of a composition comprising a biocompatible polymer, a biocompatible solvent, and a water insoluble contrast agent to the subureteral tissue of the mammal which tissue already has deposited therein with an initial amount of this composition which method comprises visualizing the position of the deposited composition in the subureteral tissue delivering a composition comprising a biocompatible polymer, a biocompatible solvent, and a contrast agent to the subureteral tissue of the mammal containing said deposited composition wherein said delivery is conducted under conditions such that additional polymer precipitate forms in situ in the subureteral tissue thereby further reducing vesicoureteral reflux in the mammal.

In the embolic compositions employed herein, the biocompatible polymer is preferably an ethylene vinyl alcohol copolymer or a cellulose acetate polymer. In a particularly preferred embodiment, the biocompatible polymer is selected to be substantially non-immunogenic.

The biocompatible solvent is preferably dimethylsulfoxide and, more preferably, anhydrous dimethylsulfoxide.

DETAILED DESCRIPTION OF THE INVENTION

This invention is directed to methods for treating vesicoureteral reflux in mammals, which methods comprise delivering a composition comprising a water insoluble biocompatible polymer and a biocompatible solvent to the subureteral region of the mammal.

Prior to discussing this invention in further detail, the following terms will first be defined:

The term "vesicoureteral reflux" refers to the retrograde movement of urine through the ureter from the bladder during voiding or with elevated pressure in the bladder. Methods for diagnosing vesicoureteral reflux are well known to those skilled in the relevant art. Such methods included, for example, intravenous pyelography, voiding cystourethrography and the like.

The terms "subureteral region" and "subureteral tissue" refer to the tissue surrounding the junction of the ureter with the bladder. As is understood in the art, the ureter is an orifice attached at its base to the bladder and permits discharge of urine into the bladder from the kidneys. Preferably, the polymeric compositions of the present invention are delivered to the subureteral region at or near the base of the ureter in the submucosal plane.

The term "water insoluble biocompatible polymer" refers to polymers which, in the amounts employed, are not appreciably soluble in water (solubility of less than 0.1 mg/mL in water at 20° C.), non-toxic, non-peptidyl, non-migratory, chemically inert, and substantially non-immunogenic when used internally in the mammal and which are substantially insoluble in the subureteral region. The biocompatible polymers do not substantially decrease in volume over time and, since the polymer forms a solid inert mass, it does not migrate to distant organs within the body. Suitable biocompatible polymers include, by way of example, cellulose acetates[10–12] (including cellulose diacetate[13]), ethylene vinyl alcohol copolymers[14,15], polyalkyl($C_1$–$C_6$) acrylates, polyalkyl alkacrylates wherein the alkyl and the alk groups contain no more than 6 carbon atoms, polyacrylonitrile and the like. Additional biocompatible polymers are disclosed in U.S. patent application Ser. No. 08/655,822 entitled "Novel Compositions for Use in Embolizing Blood Vessels" which application is incorporated herein by reference in its entirety. Further examples of biocompatible polymers are provided by Park, et al.[16] Preferably, the biocompatible polymer is also non-inflammatory when employed in vivo.

The particular biocompatible polymer employed is not critical and is selected relative to the viscosity of the resulting polymer solution, the solubility of the biocompatible polymer in the biocompatible solvent, and the like. Such factors are well within the skill of the artisan.

Preferably, the biocompatible polymers do not appreciably absorb water upon contact with the fluid of the subureteral region and typically will have an equilibrium water content of less than about 25% water and preferably less than about 15% water.

Particularly preferred biocompatible polymers include cellulose diacetate and ethylene vinyl alcohol copolymer. Cellulose diacetate polymers are either commercially available or can be prepared by art-recognized procedures. In a preferred embodiment, the number average molecular weight, as determined by gel permeation chromatography, of the cellulose diacetate composition is from about 25,000 to about 100,000; more preferably from about 50,000 to about 75,000; and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000.

As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the occlusion-forming properties of the composition. Such additional monomers include, by way of example only, maleic anhydride, styrene, propylene, acrylic acid, vinyl acetate, and the like.

Ethylene vinyl alcohol copolymers are either commercially available or can be prepared by art-recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter or needle delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative solubility of the composition in the biocompatible solvent as well as the rate of precipitation of the copolymer in an aqueous solution (e.g., plasma). In a particularly preferred embodiment, the copolymers employed herein comprise a mole percent of ethylene of from about 25 to about 60 and a mole percent of vinyl alcohol of from about 40 to about 75. More preferably, these copolymers comprise from about 40 to about 60 mole percent of vinyl alcohol and from about 60 to 40 mole percent of ethylene. These compositions provide for requisite precipitation rates suitable for treating vesicoureteral reflux in mammals.

The term "contrast agent" refers to a biocompatible (non-toxic) radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide, and barium sulfate, each of which is commercially available in the proper form for in vivo use including a particle size of about 10 $\mu$m or less. Other water insoluble contrast agents include gold, tungsten, and platinum powders.

Preferably, the contrast agent is water insoluble (i.e., has a water solubility of less than 0.01 mg/ml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the subureteral region. Preferably, the biocompatible solvent is dimethylsulfoxide. More preferably, the biocompatible solvent is anhydrous dimethylsulfoxide.

Compositions

The polymer employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer based on the total weight of the polymer composition, including contrast agent and biocompatible solvent, and more preferably from about 4 to about 5.2 weight percent. If necessary, gentle heating and stirring can be used to effect dissolution of the biocompatible polymer into the biocompatible solvent, e.g., 12 hours at 50° C.

Sufficient amounts of the optional contrast agent can then added to the solution to achieve the effective concentration for the complete polymer composition. Preferably, the polymer composition will comprise from about 10 to about 40 weight percent of the contrast agent and more preferably from about 20 to about 40 weight percent and even more preferably about 35 weight percent each based on the total weight of the polymer composition including the biocompatible polymer and the biocompatible solvent. When the contrast agent is not soluble in the biocompatible solvent, stirring is employed to effect homogeneity of the resulting suspension. In order to enhance formation of the suspension, the particle size of the contrast agent is preferably maintained at about 10 $\mu$m or less and more preferably at from about 1 to about 5 $\mu$m (e.g., an average size of about 2 $\mu$m). In one preferred embodiment, the particle size of a water insoluble contrast agent is prepared, for example, by fractionation. In such an embodiment, a water insoluble contrast agent such as tantalum having a particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under a microscope. The process is optionally repeated until a desired particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition may be heat sterilized and then stored preferably in sealed bottles (e.g., amber vials) or vials until needed.

Methods

The compositions described above are then employed in methods for treating vesicoureteral reflux in mammals. In these methods, the composition is introduced to the subureteral region via conventional catheter or needle technology using, for example, cystoscopic techniques employing, e.g., cystoscopes and ureteralscopes. Specifically, the injection may be performed through a puncture needle or cannula placed directly through the cystoscope or subureterally to the tissue adjacent to the ureter. Alternatively, the subureteral region can be exposed surgically and the composition injected directly into the tissue.

The viscosity of the formulation is preferably 30 to 100 centipoise at 20° C. and more preferably 30 to 60 centipoise. Such preferred viscosities allow for controlled, smooth injections through small bore needles or small bore catheters.

Upon discharge of the composition from the catheter or the needle into the subureteral region, the biocompatible solvent dissipates into the fluid or surrounding tissue of the subureteral region resulting in the precipitation of the water insoluble biocompatible polymer which precipitate forms a coherent mass. When a water insoluble contrast agent is employed, the coherent mass includes both the contrast agent and the water insoluble biocompatible polymer which form an integral coherent precipitate which does not separate into individual components.

The formed precipitate in the subureteral region swells (bulks) this tissue restricting the ureter orifice thus impeding the retrograde flow of urine from the bladder into the ureter.

The particular amount of polymer composition employed is dictated by the level of pre-existing support of the subureteral region, the concentration of polymer in the composition, the rate of precipitation (solids formation) of the polymer, etc. Such factors are well within the skill of the artisan. For example, individuals with weak pre-existing support of the subureteral region will require injection of more polymer composition in order to bulk up this tissue and constrict the ureter as compared to individuals with stronger pre-existing support.

The methods of this invention are particularly advantageous when a contrast agent is incorporated into the composition because this contrast agent permits, if desired, monitoring of the delivery of the biocompatible polymer while it is taking place either by fluoroscopy, ultrasound, or visually. In this way, one can ensure that the biocompatible polymer is being delivered to the optimal location in the subureteral region. As noted above, when the contrast agent is water insoluble, the contrast agent will be incorporated into the resulting precipitate (implant) which permits monitoring the size of the polymer precipitate thus-formed to ensure that it will be sufficient to block the retrograde flow of urine from the bladder into the ureter and which further permits post-injection monitoring of the implant.

Moreover, the treatment process can be modified by altering the rate of precipitation of the polymer which can be controlled merely by changing the overall hydrophobicity/hydrophilicity of the polymer. As is understood in the art, faster precipitation rates are achieved by a more hydrophobic polymer composition.

When delivery of the polymeric composition to the subureteral region is conducted via a cystoscope used in combination with a small diameter medical catheter (which typically employs a needle as described by Capozza, et al.[9]), the catheter employed is not critical provided that polymeric catheter components are compatible with the polymeric composition (i.e., the catheter components will not readily degrade in the polymer composition and none of the components of the polymer compositions will readily degrade in the presence of the catheter components). In this regard, it is preferred to use polyethylene in the catheter components because of its inertness in the presence of the polymeric composition described herein. Other materials compatible with the composition can be readily determined by the skilled artisan and include, for example, other polyolefins, fluoropolymers (e.g., polytetrafluoroethylene, perfluoroalkoxy resin, fluorinated ethylene propylene polymers), silicone, etc.

When introduced into the subureteral region, the biocompatible solvent rapidly diffuses into the fluids of this tissue leaving a solid precipitate. The precipitate is a coherent mass comprising the water insoluble biocompatible polymer and, when employed, the water insoluble contrast agent. Without being limited to any theory, it is believed that this precipitate bulks up the subureteral region thereby increasing outlet resistance to urinary flow from the bladder. This enhanced outlet resistance reduces the vesicoureteral reflux in the treated mammal.

Another advantage of this invention is that the precipitate forms a coherent mass which is substantially retained at the site of injection thereby obviating prior art concerns with migration of injected particulates into the subureteral region. Moreover, the polymeric compositions of this invention are non-biodegradable and, accordingly, do not substantially decrease in volume over time.

Still another advantage of this invention is that the polymer employed can be selected to be non-immunogenic thereby obviating concerns raised by use of collagen-type materials which can produce an immune response in vivo.

Yet another advantage of a preferred aspect of this invention is the formation of a polymeric mass in the subureteral region which mass contains a water insoluble contrast agent that permits the physician to monitor the implant over time to assure proper retention of the mass in the tissue. Additionally, if a subsequent injection is necessary to further reduce vesicoureteral reflux in the mammal, placement of the additional polymeric material is facilitated when the material previously implanted can be visualized by, for example, fluoroscopy, ultrasound, and the like. A subsequent injection can occur at any time after the initial injection including, for example, months or years later.

Utility

The methods described herein are useful in treating mammals with vesicoureteral reflux. Accordingly, these methods find use in human and other mammalian subjects requiring such treatment.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

cc=cubic centimeter
DMSO=dimethylsulfoxide
EVOH=ethylene vinyl alcohol copolymer
kg=kilogram
mg=milligram
mL=milliliter
mm=millimeter
μm=micron In the following examples, Examples 1–2 illustrate the preparation of polymer compositions useful in the methods described herein which polymer compositions comprise EVOH and cellulose acetate. Example 3 demonstrates how the methods of this invention would be employed in vivo.

Example 1

An EVOH polymer composition was prepared by combining 8 grams of EVOH (44 mole percent ethylene), 30 grams of tantalum having an average particle size of less than 10 μm (narrow size distribution), and 100 mL of anhydrous DMSO. Heating at about 50° C. for about 12 hours was used to aid dissolution. The composition was mixed until homogeneous.

Tantalum having an average particle size of less than 10 μm (narrow size distribution) was prepared by fractionation wherein tantalum, having an average particle size of less than about 20 μm, was added to ethanol (absolute) in a clean environment. Agitation of the resulting suspension was followed by settling for approximately 40 seconds to permit the larger particles to settle faster. Removal of the upper portion of the ethanol followed by separation of the liquid from the particles results in a reduction of the particle size which is confirmed under a microscope (Nikon Alphaphot™). The process was repeated, as necessary, until an average 3 μm particle size was reached.

Example 2

A cellulose diacetate polymer composition is prepared by combining 8 grams of cellulose acetate (39.7 weight percent acetyl content), 30 grams of tantalum having an average particle size of less than about 10 μm (narrow size distribution), and 100 mL of DMSO. The composition is mixed until homogeneous. Tantalum having an average particle size of about 3 μm (narrow size distribution) is prepared by fractionation as described in Example 1.

Example 3

The following example illustrates how the methods of this invention could be practiced in vivo on a mammal.

A mini-pig is selected for illustration because of similarities between porcine and human bladders and kidneys, and its small body size. First the animal is made to have incompetent, refluxing ureters by unroofing the ureters bilaterally using a standard technique of open surgery. The presence of bilateral urinary reflux is determined by conventional radiographic cystography using an iodinated contrast medium and by sonography two to three months after surgery. Excretory urography (IVP) is performed to detect any obstruction.

The animal is anesthetized with ketamine (25 mg/kg) and acepromazine (1 mg/kg) given intramuscularly. Additional anesthesia is with ketamine (25 mg/kg) and xylazine (10 mg/kg) given intramuscularly. Cystograms and an IVP are done preoperatively. With the animal in the supine position, a 15.5 Fr cystoscope is introduced into the bladder. A 22 gage needle is passed through the scope and is inserted into the suburetheral region of the left refluxing ureter. Approximately 1 to 2 mL of the composition from Example 1 above is slowly injected by hand through the needle, while lifting the ureteral orifice, under endoscopic visualization. It is advisable to wait several seconds after injection is complete before needle removal to prevent spillage of any of the composition. The ureter orifice may take on a crescent appearance after the injection. The right refluxing ureter is left untreated as a control. A cystogram, sonography (and IVP) are performed after two to three months to confirm lack of reflux in the treated ureter. Exact tissue placement of the composition is determined and monitored by conventional fluoroscopy.

From the foregoing description, various modifications and changes in the composition and method will occur to those skilled in the art. All such modifications coming within the scope of the appended claims are intended to be included therein.

What is claimed is:

1. A method for treating vesicoureteral reflux in a mammal, which method comprises delivering a composition comprising a water insoluble biocompatible polymer and a biocompatible solvent to the subureteral region of the mammal wherein said delivery is conducted under conditions such that a polymer precipitate forms in situ in the subureteral region thereby reducing the vesicoureteral reflux in the mammal.

2. The method according to claim 1 wherein said water insoluble biocompatible polymer is selected from the group consisting of cellulose acetate polymers, ethylene vinyl alcohol copolymers and polyacrylates.

3. The method according to claim 2 wherein said water insoluble biocompatible polymer is a cellulose acetate polymer or an ethylene vinyl alcohol copolymer.

4. The method according to claim 1 wherein said biocompatible solvent is selected from the group consisting of dimethylsulfoxide, ethanol, and acetone.

5. The method according to claim 4 wherein said biocompatible solvent is dimethylsulfoxide.

6. The method according to claim 1 wherein said composition further comprises a contrast agent.

7. The method according to claim 6 wherein said contrast agent is a water soluble contrast agent.

8. The method according to claim 7 wherein said water soluble contrast agent is metrizamide.

9. The method according to claim 1 wherein said composition is delivered into the subureteral tissue via a delivery means selected from the group consisting of cystoscopes, catheters and ureteralscope.

10. A method for treating vesicoureteral reflux in a mammal, which method comprises delivering a composition comprising a water insoluble biocompatible polymer, a water insoluble contrast agent and a biocompatible solvent to the subureteral region of the mammal wherein said delivery is conducted under conditions such that a polymer precipitate forms in situ in the subureteral region thereby reducing the vesicoureteral reflux in the mammal.

11. The method according to claim 10 wherein said water insoluble biocompatible polymer is selected from the group consisting of cellulose acetate polymers, ethylene vinyl alcohol copolymers and polyacrylates.

12. The method according to claim 11 wherein said water insoluble biocompatible polymer is a cellulose acetate polymer or an ethylene vinyl alcohol copolymer.

13. The method according to claim 11 wherein said biocompatible solvent is selected from the group consisting of dimethylsulfoxide, ethanol, and acetone.

14. The method according to claim 13 wherein said biocompatible solvent is dimethylsulfoxide.

15. The method according to claim 13 wherein the water insoluble contrast agent is selected from the group consisting of tantalum, tantalum oxide, and barium sulfate.

16. A method for the delivery of a composition comprising a water insoluble biocompatible polymer, a biocompatible solvent, and a water insoluble contrast agent to the subureteral tissue of the mammal which tissue already has deposited therein with an initial amount of this composition which method comprises visualizing the position of the deposited composition in the subureteral tissue delivering a composition comprising a biocompatible polymer, a biocompatible solvent, and a contrast agent to the subureteral tissue of the mammal containing said deposited composition wherein said delivery is conducted under conditions such that additional polymer precipitate forms in situ in the subureteral tissue thereby further reducing vesicoureteral reflux in the mammal.

17. The method according to claim 16 wherein visualization is conducted by direct visualization, fluoroscopy or ultrasound.

18. The method according to claim 16 wherein said water insoluble biocompatible polymer is selected from the group consisting of cellulose acetate polymers, ethylene vinyl alcohol copolymers and polyacrylates.

19. The method according to claim 18 wherein said water insoluble biocompatible polymer is a cellulose acetate polymer or an ethylene vinyl alcohol copolymer.

20. The method according to claim 18 wherein said biocompatible solvent is selected from the group consisting of dimethylsulfoxide, ethanol, and acetone.

21. The method according to claim 20 wherein said biocompatible solvent is dimethylsulfoxide.

22. The method according to claim 20 wherein the water insoluble contrast agent is selected from the group consisting of tantalum, tantalum oxide, and barium sulfate.

* * * * *